United States Patent
Batchelder (10) Patent No.: US 6,507,393 B2
(45) Date of Patent: Jan. 14, 2003

(54) SURFACE CLEANING AND PARTICLE COUNTING

(76) Inventor: John Samuel Batchelder, 2 Campbell Dr., Somers, NY (US) 10589

( * ) Notice: Subject to any disclaimer, the term of this patent is extended or adjusted under 35 U.S.C. 154(b) by 0 days.

(21) Appl. No.: 10/067,555

(22) Filed: Feb. 5, 2002

(65) Prior Publication Data

US 2002/0071115 A1 Jun. 13, 2002

Related U.S. Application Data

(63) Continuation-in-part of application No. 09/310,491, filed on May 12, 1999.

(51) Int. Cl.[7] ............................................... G01N 21/00
(52) U.S. Cl. ................. 356/237.1; 356/440; 356/239.8; 356/238.3; 356/237.3; 399/101; 399/139; 399/327; 101/463.1; 355/15; 355/14 D; 355/246; 427/202; 427/368
(58) Field of Search ........................... 356/237.1, 237.2, 356/237.3, 237.4, 237.5, 237.6; 399/101, 138, 139, 327; 355/14 D, 15, 246; 427/202, 368; 100/463.1

(56) References Cited

U.S. PATENT DOCUMENTS

| | | | | |
|---|---|---|---|---|
| 3,999,481 A | * | 12/1976 | Sankus, Jr. ............... | 101/463.1 |
| 4,009,047 A | | 2/1977 | Lindsay ........................ | 355/15 |
| 4,272,182 A | * | 6/1981 | Abe et al. ................. | 355/14 D |
| 4,331,712 A | * | 5/1982 | Cohen et al. ............... | 427/202 |
| 4,607,947 A | * | 8/1986 | Ensing et al. ................. | 355/15 |
| 4,705,388 A | | 11/1987 | Huntjens ..................... | 355/15 |
| 4,998,141 A | * | 3/1991 | Altmann ..................... | 356/440 |
| 5,848,332 A | * | 12/1998 | Machida ..................... | 399/139 |
| 5,902,678 A | | 5/1999 | Kondo ........................ | 428/345 |
| 6,023,597 A | | 2/2000 | Mayuzumi ................. | 399/176 |
| 6,201,940 B1 | * | 3/2001 | Lee ............................ | 399/101 |
| 6,360,073 B1 | * | 3/2002 | Eelen ........................ | 399/327 |

* cited by examiner

Primary Examiner—Frank G. Font
Assistant Examiner—Sang H. Nguyen (57) ABSTRACT

A method and an apparatus for detecting removable particulates initially on a test surface or surface to be inspected. The removable particles are transferred to a portion of a tacky surface on a carrier by adhering and then removing the portion of the tacky surface from the test surface. The carrier is received by a positioning means and passed through the field of view of a surface inspection means guided by a controller. Signals from the surface inspection means are combined with coordinates from the controller to produce particle coordinates, which indicate particulates initially on the test surface. Particle coordinates on the tacky surface measured before the tacky surface is adhered and removed from the test surface can be compared with particle coordinates measured after the tacky surface is adhered and removed from the test surface. Several test surfaces can be sequentially inspected using the same carrier by storing particle coordinates after each measurement and comparing the most recent measurement with the cumulative previous measurements. The tacky surface and the associated particle coordinates can be conveyed to other analytical instruments for subsequent analysis.

13 Claims, 11 Drawing Sheets

Section A

Fig. 12b

Section B

SURFACE CLEANING AND PARTICLE COUNTING

RELATED APPLICATIONS

This is a continuation in part of application Ser. No. 09/310,491, filed May 12, 1999, which is incorporated herein in its entirety.

FIELD AND BACKGROUND OF THE INVENTION

This invention relates to controlling particulate contamination on surfaces of products, machine tools, and work areas. More particularly, the invention relates to measuring the removable particulate contamination on surfaces in semiconductor manufacturing, data storage manufacturing, fluid filter inspection, display manufacturing, clean rooms, manufacturing, aerospace manufacturing, and health care industries.

Quantified measurements of particulate contamination can comprise a total number of particles detected on the inspected surface, a total number of particles per area of the inspected surface, a size histogram of the total number of particles detected per area of the inspected surface, a cumulative particulate volume or area, or a combination of these measurements. Surface particle contamination measurements are generally performed by light scattering or image analysis.

U.S. Pat. Nos. 4,898,471 and 5,343,290 describe surface particle contamination measurements optimized for inspecting semiconductor wafers.

U.S. Pat. No. 4,766,324 describes comparing two scans of the same monitor wafer to determine particles added to or removed from the wafer between the two scans.

This invention also relates to removing particulates from surfaces. More particularly, the invention relates to cleaning processes to remove particulate contamination which are used in manufacturing systems to prevent localized defects, to prevent optical or beam scattering, prevent cross contamination of processing materials, to allow close mating of surfaces, to remove magnetic contaminants, and to sanitize surfaces. Surface particle removal is generally performed with the use of solvents, fluid shear, ultrasonics, transfer to a tacky surface, or mechanical agitation.

U.S. Pat. No. 4,009,047 describes contacting a sheet to be cleaned with a tacky roller.

U.S. Pat. No. 4,705,388 describes determining when a web-cleaning tack roller requires rejuvenation by measuring the optical reflectivity of the roller.

U.S. Pat. No. 5,373,365 describes measuring the reflectivity of a web-cleaning roller, and from that inferring the contamination level on the roller.

U.S. Pat. No. 5,671,119 describes cleaning an electrostatic chuck in a semiconductor process tool by adhering and removing a dummy tacky wafer to the chuck.

U.S. Pat. No. 5,902,678 describes cleaning a surface by applying an anti-static pressure sensitive film to a surface, irradiating the film with ultraviolet light, and removing the film.

U.S. Pat. No. 6,023,597 describes a method for forming a conformable anti-static roller.

Teknek Electronics Limited of Inchinnan, Scotland, makes printed circuit board cleaning products that first contact the circuit board with a conformal rubber roller, and then contact the rubber roller with an adhesive coated roller.

This invention further relates to combining cleaning a surface and to measuring the removable particulates on that surface. Combining these processes is useful for inspecting surfaces that are otherwise difficult to inspect by currently available techniques because the surfaces are too rough, optically scattering, or large. They are also useful because they combine a cleaning process that adds value to a product with a measurement that improves the control of the process.

U.S. Pat. No. 5,253,538 is embodied in the product QIII® available from Pentagon Technologies of Freemont, Calif. It describes inspecting a planar surface for particulates by shearing gas across the surface using a nozzle assembly, and subsequently inspecting that gas using an airborne particle counter.

U.S. Pat. No. 5,939,647 describes a system similar to a QIII for planar surface inspection in which the sampling head is attached to a handle by a gimbal.

U.S. Pat. No. 6,269,703 describes releasing particles from a surface using a fluid applied to shear across the surface. The fluid is then inspected for particulates.

The Surfex product from Particle Measuring Systems of Boulder, Co, inspects surfaces by ultrasonic cleaning in an aqueous bath followed by inspection of the water by a liquid particle counter.

This invention further relates to retaining particulates removed from a surface on a carrier, determining the locations of the particles on the carrier, and passing the carrier and the locations of the particles on the carrier to other analytical instruments like electron microscopes, optical review stations, and x-ray absorption. Retaining the found particles gives tracability to the measurement technique. It allows follow up analysis to be performed on archived carriers to analyze product failure mechanisms and process changes.

U.S. Pat. No. 5,655,029 describes detecting a region of interest on a specimen with one microscope and conveying the specimen and the coordinates to a second microscope for automated review.

It would be desirable to provide a combination of surface particulate removal and particle measurement that would not scuff, abrade, or otherwise interact with the surface to generate more contamination. It would be desirable that the technique would not require the immersion of the surface in a solvent, allowing inspection of large, or vertically oriented, or solvent sensitive surfaces. It would be desirable that the technique would clean and inspect complex, rough, or non-planar surfaces. It would be desirable that the technique would inspect and clean interior surface of manufacturing tools with limited or confined access. It would be desirable that particulates that have been removed and detected from a surface would subsequently be analyzable by alternative analytical instruments.

DISCLOSURE OF INVENTION

This invention is a method and an apparatus that detects removable particulates initially on a test surface or a surface to be inspected. The removable particles are transferred to a portion of a tacky surface on a carrier by adhering and then removing the portion of the tacky surface from the test surface. The carrier is received by a positioning means and passed through the field of view of a surface inspection means guided by a controller. Signals from the surface inspection means are combined with coordinates from the controller to produce particle coordinates, which indicate particulates initially on the test surface. Particle coordinates on the tacky surface measured before the tacky surface is adhered and removed from the test surface can be compared with particle coordinates measured after the tacky surface is adhered and removed from the test surface. Several test surfaces can be sequentially inspected using the same carrier by storing particle coordinates after each measurement and comparing the most recent measurement with the cumulative previous measurements. The carrier and the associated particle coordinates can be conveyed to other analytical instruments for subsequent analysis.

BRIEF DESCRIPTION OF DRAWINGS

FIG. 12b is a cross section view referencing FIG. 12a.

FIG. 12c is a cross section view referencing FIG. 12a.

DESCRIPTION OF A PREFERRED EMBODIMENT

Tacky Surface

Particulate contamination can differ from other features of a surface in that there is an interface between the particulate and the original surface. If the adhesion at that interface is comparable to the cohesion of the surface material, the particle is so firmly adhered that it will not likely be removed later to become particulate contamination in some process or apparatus. If the adhesion is weak enough that the particle is removable, the particle is of more interest for contamination control.

For specificity and brevity we will subsequently describe as 'tacky' a surface that has been engineered to removably adhere to the surface being inspected. The degree of adhesion depends on many factors, including surface energies of the tacky surface and the surface to be inspected, adsorbed liquid layers on those surfaces, adsorbed molecular contamination on those surfaces, contact time and pressure between the surfaces, the ambient temperature, the compliance of both surfaces, mechanical interlocking due to roughness of both surfaces, inter-diffusion, and chemical reactions. Generally higher adhesive forces between the tacky surface and a particle will remove a larger fraction of the particle population on a surface. A tacky surface with too strong an adhesive bond to the test surface can cause failure mechanisms such as depositing portions of that surface on the test surface, or forming permanent adhesion of the entire surface to the test surface.

Tacky surfaces for high surface energy test surfaces such as the native oxide found on silicon monitor wafers need to have relatively low adhesion forces, so that the adhesion between the test surface and the tacky surface does not exceed the cohesive forces within the tacky surface. The tacky surface found on clean room removable tape model 1310 from the UltraTape Industries of Oregon, US, shows good particle removal without residue when used on monitor silicon wafers. A higher tack such as that found on model 4658F tape from the 3M Company of Minnesota, US, is appropriate for lower surface energy test surfaces such as polycarbonate. U.S. Pat. No. 5,902,678 describes a pressure sensitive adhesive on a flexible backing that demonstrates good particle removal characteristics. U.S. Pat. No. 5,187,007 describes a pressure sensitive adhesive used in wafer dicing; the characteristics of this film make it useful as a tacky surface in the following embodiments. The tacky films sold by Gel-Pak Corporation predictably adhere and cleanly release from test surfaces. Preferred embodiments for the tacky material include acrylic or methacrylic adhesive, a silicone pressure sensitive adhesive, and a rubber pressure sensitive adhesive. Preferred additives to the tacky material include additives to improve ionic and electronic conduction of the tacky material so that it can dissipate static electricity; a useful maximum resistivity for the tacky surface is 1012 ohms per square centimeter. Those skilled in the art will appreciate that there is a spectrum of possible compositions for the tacky surface, and that a particular test surface may require a specialized tacky surface.

Small particles are difficult to detect on most tacky surfaces, compared to other surfaces such as monitor silicon wafers, for a variety of reasons. Tacky surfaces are generally not strongly absorbing or reflective for optical inspection, so that light emerges after scattering from sub-surface features, contaminants, or variations in index of refraction. The surfaces are generally not globally smooth, but have localized height variations that require small fields of view in order to maintain focus. The surfaces are generally not locally smooth, so that grazing illumination or Lloyd's mirror collection is necessary to reduce surface scatter. The large molecular weights of the bulk constituents are difficult to filter, so that there are particulates below the tacky surface that can flicker in and out of detection depending on the precise focus position with respect to the surface. Index variations in the bulk material can generate relatively high levels of background light scatter.

System

Figure 1:
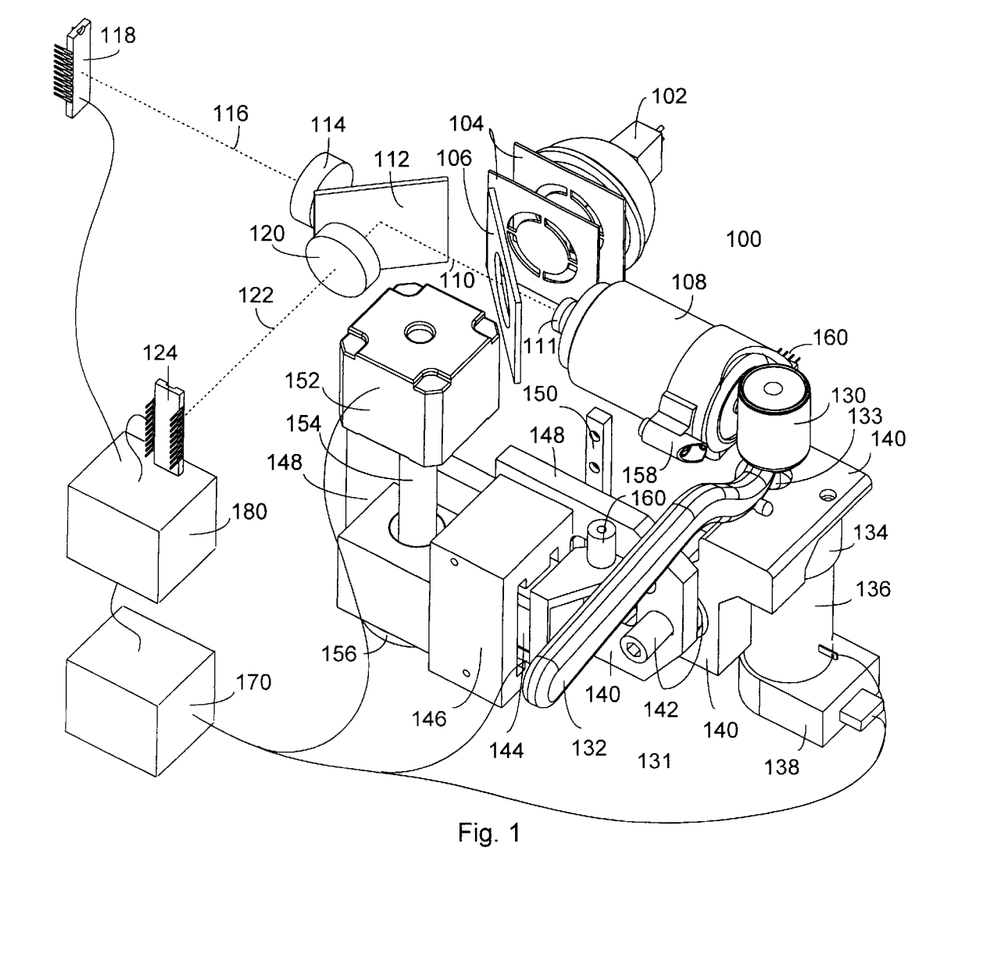
FIG. 1 is a perspective view of a preferred embodiment of the apparatus.

FIG. 1 shows the preferred embodiment of the invention, in which the carrier with the tacky surface (130) is mounted on a positioning means (131) in the field of view of a surface inspection means (100). The carrier can be inspected before it has be adhered to and removed from a test surface, after being applied to a first test surface, or after being applied to several test surfaces in succession.

The surface inspection means (100) of this embodiment is an automated darkfield optical microscope. Light from a halogen lamp (102) is spatially filtered by baffles (104) and reflected by a ring mirror (106) so mostly collimated light fills the darkfield illumination mirror of the objective (108). The objective (108) is mounted to a frame that has been omitted for clarity. The illumination is incident on the tacky surface (130) at nearly grazing angles. Scattered light from the tacky surface (130) is imaged by the darkfield objective (108) through filter (111), a beam splitter (112), a first tube lens (114) onto a linear CCD detector array (118), and a second tube lens (120) onto a second linear CCD detector array (124). The detectors (118 and 124) transmit intensity (I) and X coordinate information to analysis electronics (180). The first tube lens (1 14) and detector array (118) is imaged to a plane at the tacky sheet that is within approximately three depths of focus of the tacky surface. If the second tube lens (120) and detector array (124) is utilized, it should be imaged at least one depth of focus farther from the tacky surface and deeper into the bulk material supporting the tacky surface than the first lens and detector array. If the second tube lens and detector array is not utilized the beam splitter (112) should be removed; this is a preferred embodiment for tacky surfaces with very low bulk contamination and scattering. The carrier of the tacky surface (130) is attached to a handle means (132); this combination will be subsequently discussed in more detail.

Small particles scatter shorter wavelengths more strongly, so optical sources with more short wavelength energy are preferred. Alternative preferred embodiments for illumination include an arc lamp, light emitting diodes, and a laser. Incoherent illumination typically generates less noise in the detected image than coherent illumination. An objective with a numerical aperture between 0.5 and 0.95 is preferred to restrict the depth over which particles can be detected. Immersion optics is not preferred, since particles can be nearly index matched to the immersion fluid. The second detector array can be omitted if the bulk material supporting the tacky surface is generally free of localized light scattering, and the thickness of the bulk material is at least eight depths of focus. Alternative preferred embodiments for the detectors include CMOS linear arrays, CCD and CMOS two dimensional arrays, TDI arrays, and position sensing photomultipliers.

The handle means (132) is received by the positioning means (131), which passes the tacky surface (130) through the field of view of the surface inspection means (100). The carrier of the tacky surface (130) mates with a spindle (133) attached to a gear reducer (134), servo motor (136), and encoder (138); these rotate the carrier of the tacky surface (130) under the control of a controller (170); we will refer to this degree of freedom as θ motion of the carrier with respect to the objective. The gear reducer (134) mounts on a pivoting bracket (140) attached to an elevator plate (148) by a stud bearing (142). A rotary voice coil frame (146) attaches to the elevator plate (148), and the moving voice coil (144) attaches to the pivoting bracket (140), allowing the carrier to be rapidly moved towards and away from the darkfield objective under the control of a controller (170); we will refer to this degree of freedom as Z motion of the carrier with respect to the objective. The elevator plate (148) is moved by a microstepping motor (152) acting through a leadscrew (154) and nut (156) under the control of a controller (170); we will refer to this degree of freedom as ord motion of the carrier with respect to the objective. An optical focus detector consisting of a grazing laser source (158) and sensor (160) allows the controller to monitor the relative position $Z_{opt}$ of the detector images with respect to the tacky surface (130), and will be discussed in more detail. An LVDT sensor (160) affixed to the elevator plate (148) allows the controller (170) to monitor the absolute position $Z_{lab}$. The controller (170) provides real time position information (θ, ord, $Z_{lab}$, $Z_{opt}$) to the analysis electronics (180).

Additional preferred embodiments for generating the θ motion also include air bearings, microsteppers, brushless motors, and DC motors. Additional preferred embodiments for the ord and Z motion include flexures, air bearings, linear bearings, squeeze bearings, inchworms, piezoelectric transducers, linear voice coils, and leadscrews. Additional preferred embodiments for monitoring θX, Y, and $Z_{lab}$ include capacitive sensors, incremental optical sensors, air gages, eddy current sensors, inductance sensors, and optical displacement sensors. The controller is preferably one or more real time microcontrollers. The analysis electronics is preferably a combination of analog pre-processing, ASICs, FPGAs, CPLDs, FIFOs, RAM, one or more general purpose processors, magnetic disk, removable storage, and communication capability.

Less preferred embodiments of the surface inspection means (100) include non-optical measurement techniques such as scanning electron microscopy, atomic force microscopy, an acoustic microscopy. In some applications sensitivity will be enhanced by condensing vapor preferentially on the particles transferred to the tacky surface from a saturated atmosphere.

Figure 2A:
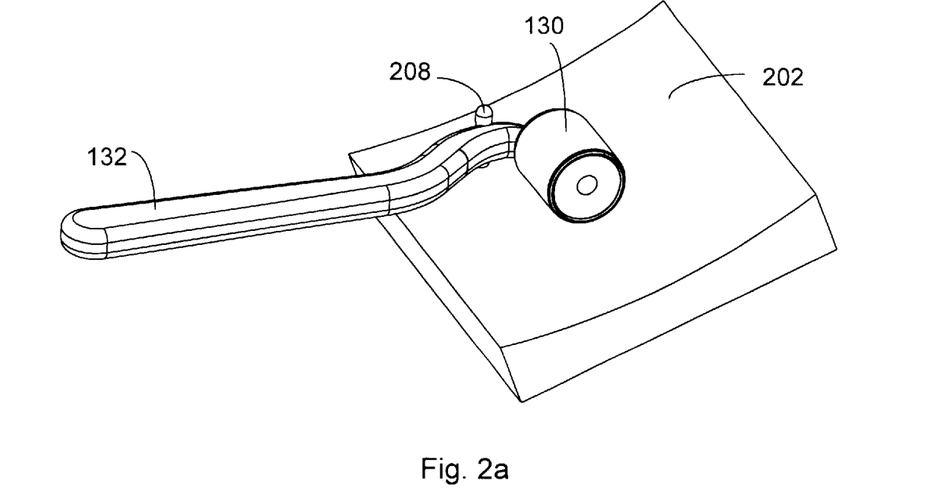
FIG. 2a is a perspective view of a handle means applying a carrier of a tacky surface to a non-planar test surface.
Figure 2B:
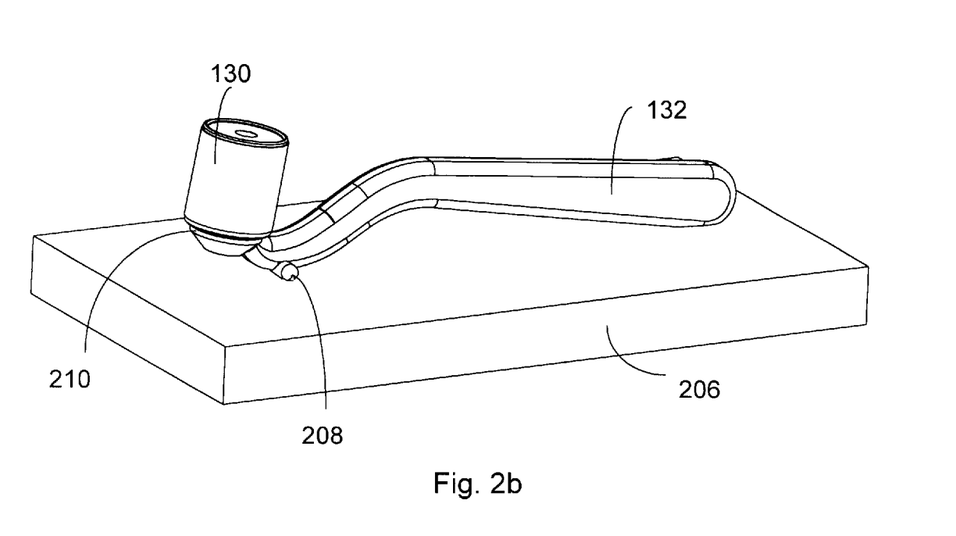
FIG. 2b is a perspective view of a handle means attached to a carrier of a tacky surface.
Figure 3:
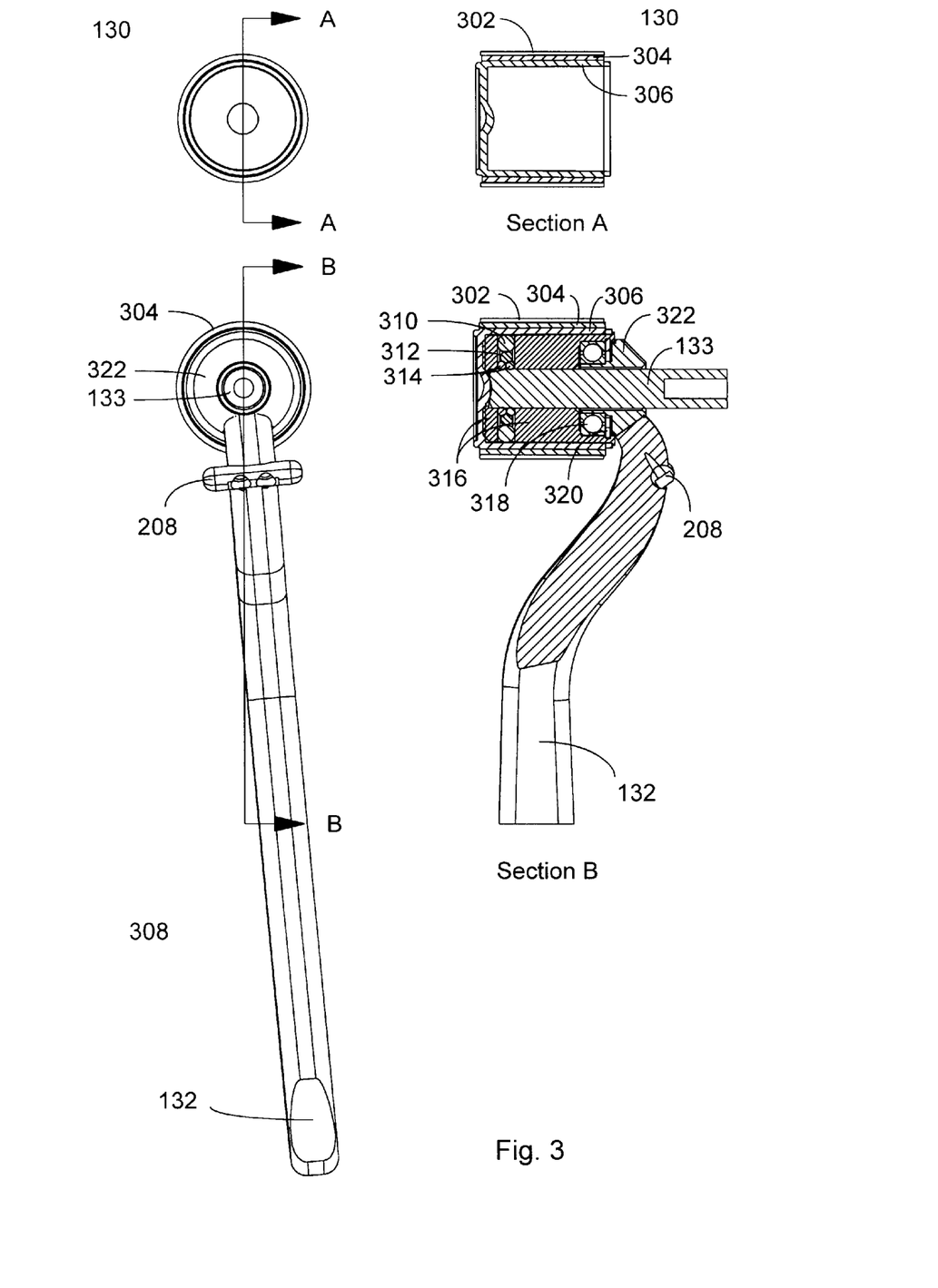
FIG. 3 is a perspective and cross sectional view of a carrier of a tacky surface, and of a handle means attached to a carrier of a tacky surface.

FIGS. 2 and 3 describe the carrier of the tacky sheet (130) and the handle means (132) in more detail. In the most preferred embodiment the surface of the tacky sheet is generally cylindrical; this allows non-planar surfaces to be inspected, as shown in FIG. 2a. FIG. 2b shows the handle means (132) with the attached carrier of the tacky sheet (130) in an idle position resting on a slab (206). A pin (208) provides stability. A rotary joint (210) allows the carrier of the tacky sheet (130) to rotate freely with respect to the handle (132).

A detail of the carrier of the tacky sheet (130) is shown in the top view and its associated cross section A of FIG. 3. The rigid core of the carrier is a plastic cylinder with a closed end (306). A layer of UltraTape 1310 (302) provides the external tacky surface. A layer of Dupont 4949 black very high bonding tape (304) provides an optically absorbing backing as well as comformality. A conformal support layer under the tacky surface improves wetting of the tacky surface with the test surface. It also allows a generally cylindrical tacky surface to intimately contact a test surface whose one principle radius of curvature lies in a plane which is not orthogonal to the axis of the cylindrical surface. It also allows a generally tacky surface to intimately contact a test surface that has two radii of curvature.

A detail of the carrier of the tacky sheet (130) and its attachment to the handle means (308) is shown in the bottom view and its associated cross section B of FIG. 3. A bobbin (316) is connected to a button (322) with a sealed bearing (318) and a C-ring (320). The handle (132) attaches to the button (322) using screws passing through the pin (208). The spindle (133) from the positioning means (131) mates with a close tolerance hole in the bobbin (316). Elastomeric o-rings (314) provide traction so that the bobbin (316) can be easily manually inserted and removed on the spindle (133) but that the bobbin does not slip on the spindle when the positioning means (131) applies torque to the spindle. The plastic core (306) slides over the bobbin; the opening of the plastic core mates with a lip on the bobbin, and eight captured metal balls (310) in the bobbin (316) apply centering force outwards on the inner surface of the plastic core (306), resulting from pressure from a captured o-ring (310). The handle means should generate as close to zero contamination as possible; the closed end of the plastic core (306) helps to contain particles that may be generated by the rolling and receiving processes. Alternative preferred embodiments of the carrier of the tacky sheet (130) will be subsequently described. Less preferred embodiments for mechanically mating the spindle with the handle means include a tapered pin and hole, a bayonet mount, a screw and nut, a shaft with a keyway, and a shaft with a detent.

Figure 4:
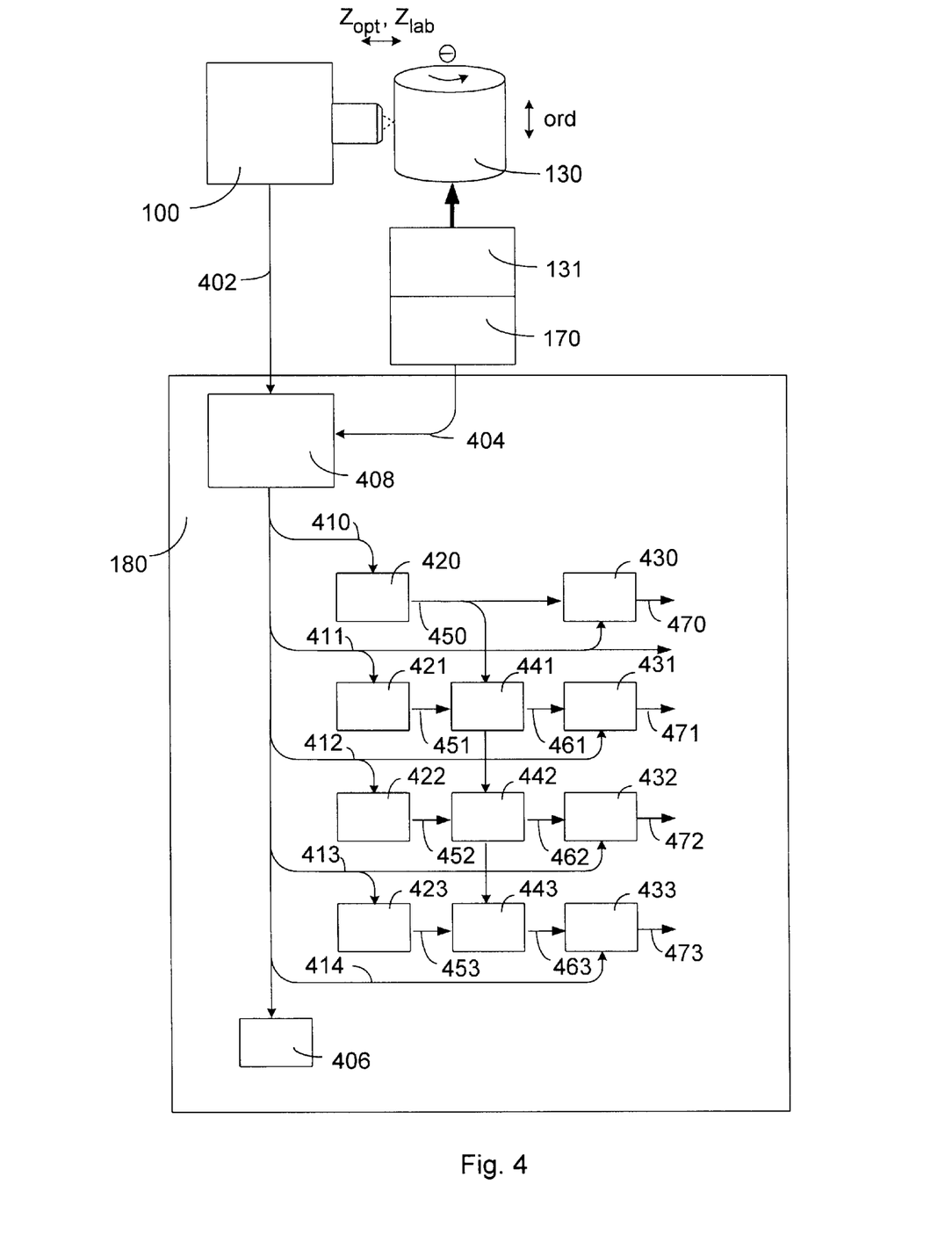
FIG. 4 is a data flow diagram showing data transfer paths between calculation means.

FIG. 4 shows the data flow of the most preferred embodiment. The carrier of the tacky sheet (130) is scanned through the field of view of the surface inspection means (100) by the positioning means (131) as directed by a controller (170). Particle signal coordinates comprise light scatter intensity (I) and X position information (402), and are generated by the surface inspection means (100) and sent to the analysis electronics (180). ($\theta$, ord, $Z_{opt}$, $Z_{lab}$) position information (404) and are sent to the analysis electronics (180), and are combined with particle signal coordinates (402) in a first calculation means (408) to generate particle coordinates (I, abs, ord, Z) in the coordinates of the carrier of the tacky surface (130). The details of the first calculation means will be subsequently described. The output of the first calculation means is labeled differently in FIG. 4 for the different instances that the carrier of the tacky sheet (130) is inspected. Particle data resulting from a scan prior to adhering and removing the tacky sheet from the test surface is (410). Particle data from a scan after adhering and removing the tacky sheet from the test surface is (411). Particle data following adhering and removing the tacky sheet from subsequent test surfaces are (412), (413), and (414); these subsequent test surface could be repeated measurements of the original test surface, but are more likely measurements of alternate test surfaces. In principle an arbitrary number of clean test surfaces can be so inspected with a single carrier attached to a tacky surface; in practice the number of repeated uses is limited primarily by the accumulation of contamination on the tacky surface. In the simplest preferred embodiment, there is no prior scan (410); the particle coordinates (411), generated while scanning a tacky surface that has been applied to and removed from the test surface, are assumed to represent particles transferred from the test surface; this represents an upper limit to the number of particles transferred from the test surface. In the most preferred embodiment the prior scan (410) is stored in a first memory means (420). A second calculation means (430) identifies particles that were transferred from the test surface (470) as those particle coordinates from (411) that have no corresponding particle coordinates from the stored previous scan (450). To re-use the tacky surface, a second memory means (421) stores the scan data (411), a third calculation means (441) combines particle data from the first and second memory means (450) and (451) to form (461), and an instances of the second calculation means (431) identifies particles that were transferred from the second test surface (471) as those particle coordinates from (412) that have no corresponding particle coordinates in (461). Two additional test surfaces can be measured using third memory means (422) and fourth memory means (423), instances of the third calculation means (442) and (443), and instances of the second calculation means (432) and (433), generating the outputs (472) and (473). Further repetitions are calculated in a similar manner. The particle data is stored in a removable storage medium (406) such as a writable CD ROM or DVD, so that it can later be transferred to a separate analytical instrument.

In the most preferred embodiment the first calculation means utilizes a convolution filter to improve the contrast of a pixel compared to its immediate surroundings. Corrections are applied for fixed pattern noise and gain variations in the detector arrays. Small pixel sizes improve the contrast of particles compared to surface roughness and bulk subsurface scatter, so that high speed detector arrays and pipelined analysis hardware is preferred. The output of the calculation means can be transmitted to an operator by a display, a printout, or an enunciator. The output of the calculation means can be communicated to a WAN or LAN through a variety of interfaces known to those skilled in the art.

Figure 5:
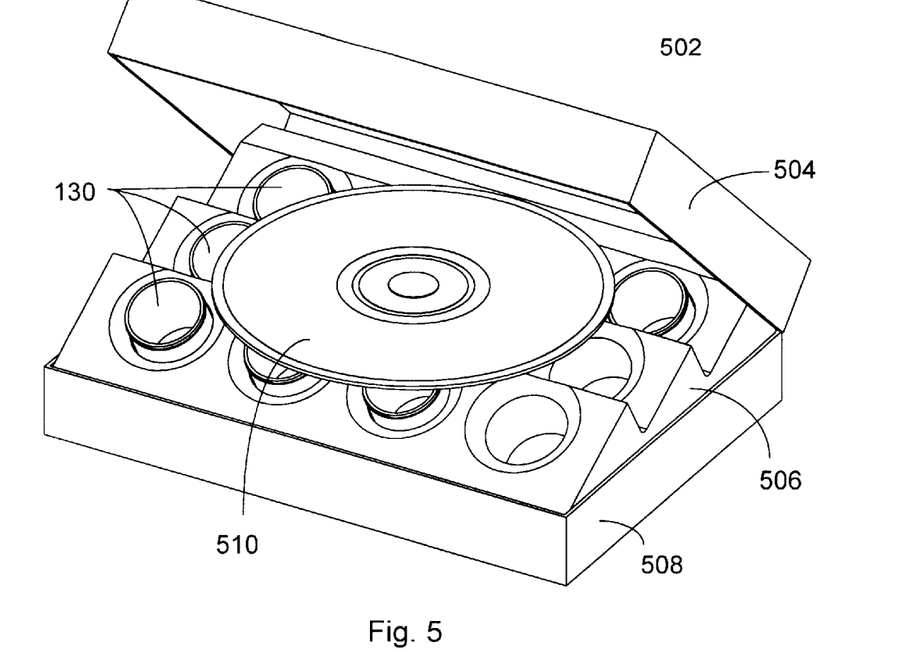
FIG. 5 is a perspective view of a box for transporting several carriers and a removable data storage element.

FIG. 5 shows how carriers of the tacky surface (130) could be packaged for use with the surface inspection means (100) and the handle means (308). Several carriers are stored in individual compartments formed in a molded sheet (506) contained in a box formed by a bottom (508) and a hinged top (504). The carriers are angled to allow the handle means (308) to engage any carrier while in its individual compartment. After a carrier had been used, its compartment becomes the archival storage location for the carrier. A writable CD (510) resides on a post formed in the molded sheet; the CD serves as the removable storage medium for any of the carriers in the box.

Figure 6:
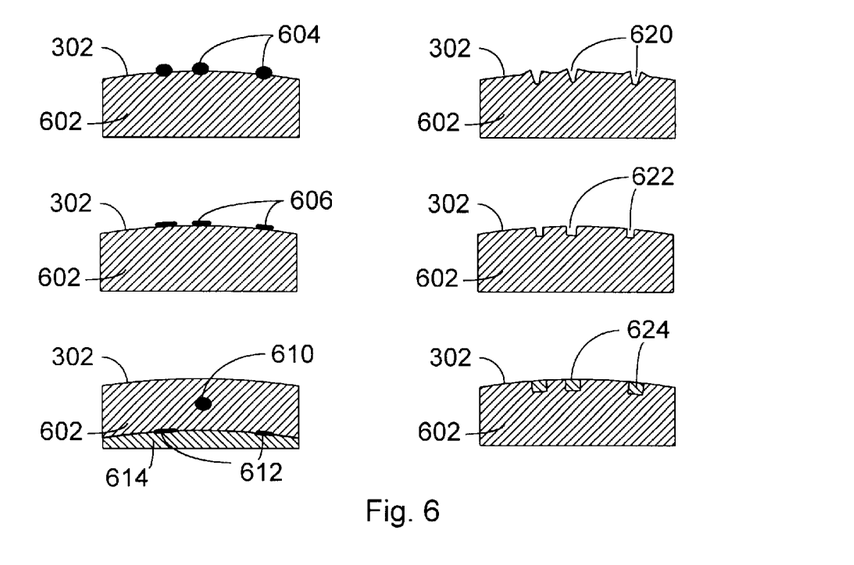
FIG. 6 shows several types of alignment marks proximate to the tacky surface.

FIG. 6 shows six configurations for alignment marks proximate to the tacky surface. These alignment marks are selected so that they scatter light and are detectable by the surface inspection means. Particulates such as metallic or latex spheres (604) can be deposited on top of the tacky surface, or they can be pressed somewhat into the bulk of the tacky material (602). Carbon black can be electrophotographically deposited, or inks can be jetted or silkscreened to form the alignment marks (606). Often the tacky bulk material (602) is doctored, dipped, or spray coated onto a supporting substrate (614); in this case the alignment marks can be pre-deposited on the buried surface of (614) prior to the application of the tacky material. Alignment marks can comprise naturally occurring scattering features on the tacky surface, in the bulk of the tacky material (610), or on the back surface of the tacky material. The surface of the tacky material can be distorted with scribe lines or stylus marks (620). The most preferred embodiment is to cleanly ablate small pockets (622) in the tacky surface using a localized energy source like an excimer laser. A UV light source can change the cross linking of localized volumes embedded in the surface (624), causing index of refraction variations that can scatter light. In less preferred embodiments, alignment marks can be utilized that require additional detection means, such as magnetization patterns, sprocket holes, and oriented gratings.

Figure 7:
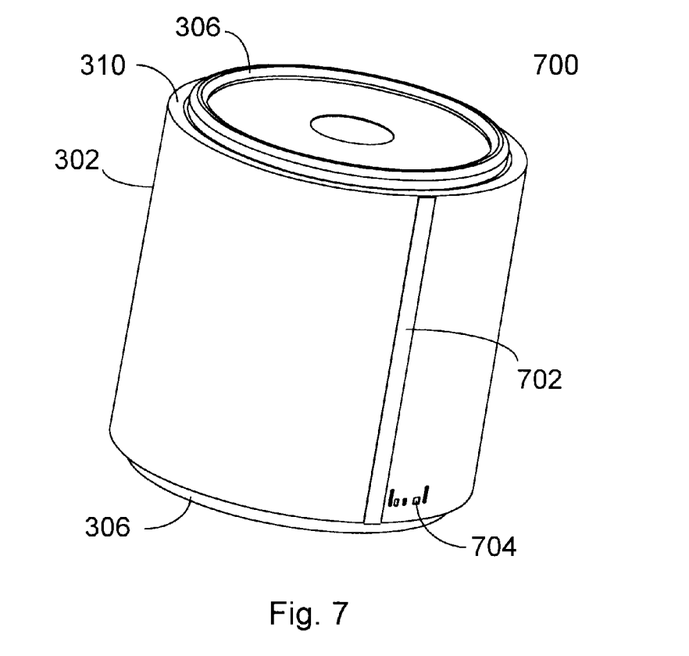
FIG. 7 shows a perspective view of the most preferred embodiment of a carrier of a tacky surface with a pattern of alignment marks and a low tack strip.

For any of the embodiments that require repeated inspection of the tacky surface, the alignment marks can be used to translate coordinate systems so that the handle means can be re-installed in a random orientation. Since the shape and pattern of alignment marks is known, the location of the alignment marks can be used as an input to the first calculation means (180) for appropriately translating each data scan. FIG. 7 is the most preferred embodiment of the invention. FIG. 7 shows a preferred configuration for alignment marks (704). The most preferred embodiment utilizes a sequence of alignment marks in a pattern analogous to a bar code. The locations of some marks in the code indicate the orientation of the surface. Other types of information can also be contained in the code, such as a serial number, an expiration date, and the composition of the surface.

The carrier of the tacky surface in FIG. 7 (700) has an additional feature. A strip of non-tacky material (702) spans the length of the tacky surface, so that there is a small range of rotation angles of the rotary joint for which only the non-tacky surface (702) will be in contact with the test surface. For these orientations of the rotary joint, the carrier of the tacky surface can be easily lifted off of the test surface. This is useful to limit the shear forces on the tacky sheet to eliminate cohesive failure of the tacky material. It is also useful in reducing the forces applied to the handle means and the test surface.

Figure 8:
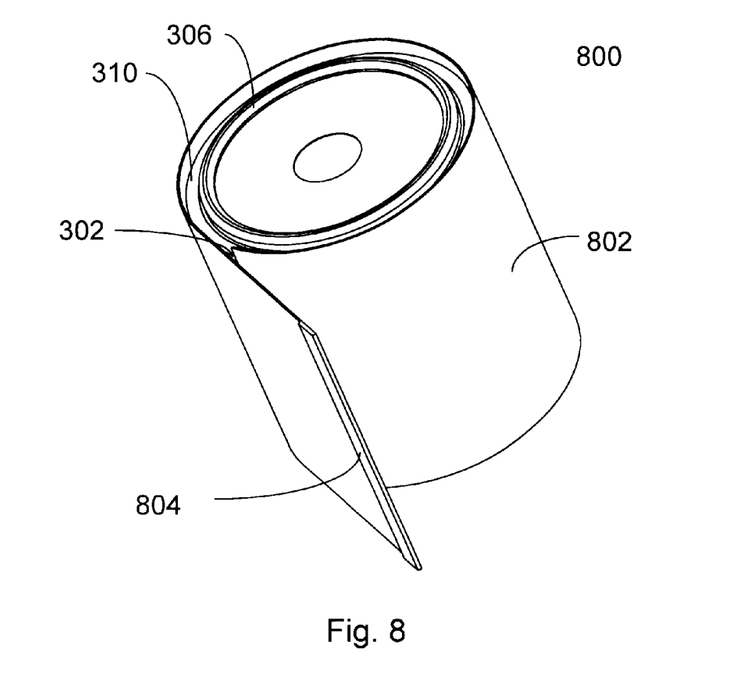
FIG. 8 shows a perspective view of a carrier of a tacky surface with a protective covering.

FIG. 8 shows a protective film (802) wrapped around the carrier of the tacky surface (130). In the most preferred embodiment the outer surface of this protective film is also tacky; this aids in storing and replacing the film after the carrier has be used. A color-coded tag (804) aids in starting the removal of the protective film. Additionally a conformal coating can be applied to the assembly of the carrier and the additional conformal, tacky, and protective layers; this seals the edges of the layers and captures contaminants that may have formed on those edges during manufacturing of the assembly.

Figure 9:
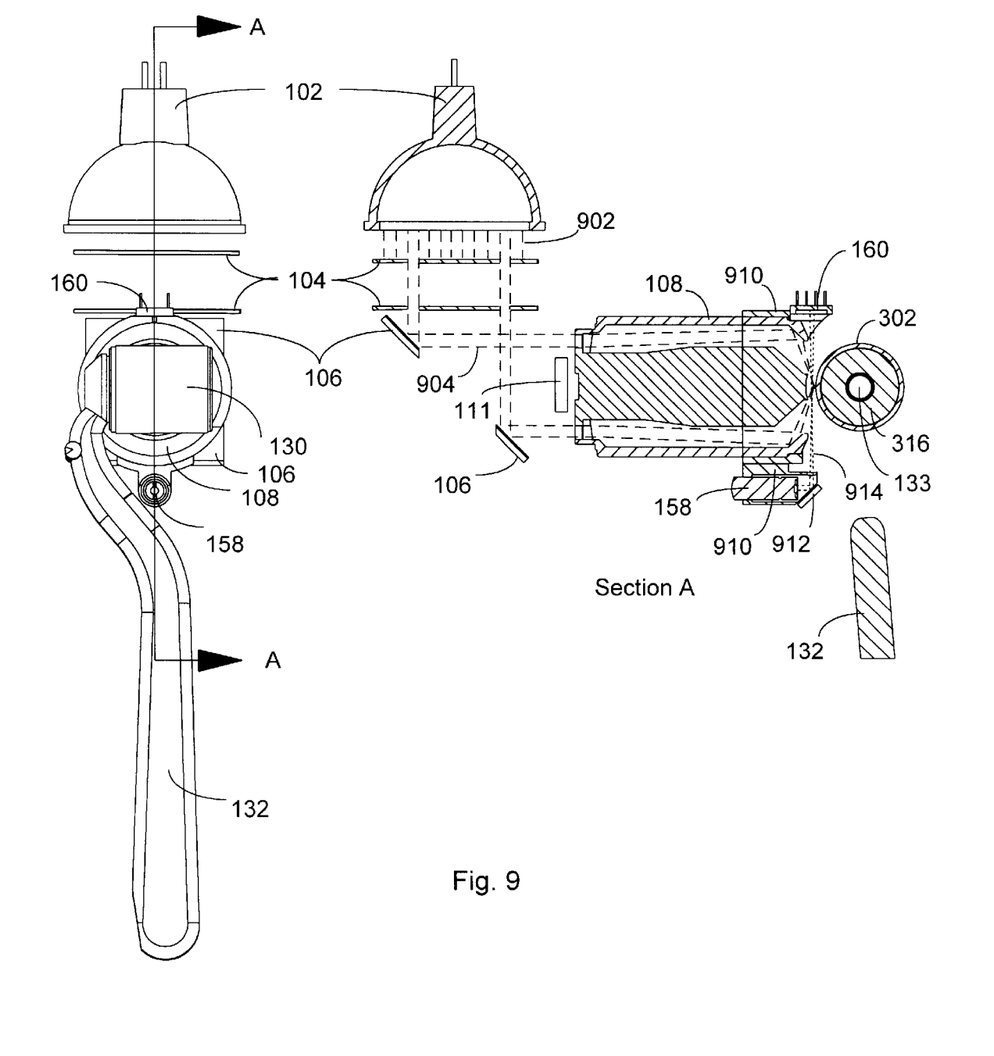
FIG. 9 show a plan view and a cross section of the illumination, focus position detection, and handle means of a preferred embodiment.

FIG. 9 shows a view of the handle means, the carrier of the tacky surface (130), the illumination, the objective, and the focus sensor. As previously describe, light (902) from the halogen bulb (102) is partially blocked by baffles (106) to form a collimated annular ring (904), which is reflected towards the grazing angle mirror of the objective (108) by a ring mirror (106). The illumination is incident on the surface outside of the collection cone of the objective (108); in the most preferred embodiment the angle of illumination should be between 70 and 90 degrees. The focus detector comprises a solid state laser (158), a mirror (912), a linear CMOS sensor array (160), and a mounting ring (910). The collimation of the laser is adjusted so that the laser beam comes to a focus approximately on the axis of the objective (108). Adjustment screws in the mounting ring (910) are used to align the laser so that the focus spot crosses the axis of the objective approximately at the image of the first detector array (118). The convex tacky surface acts as a modified knife edge test; as the surface moves towards the objective, the laser light reaching the CMOS array is both diminished and deflected towards linear sensor elements that are progressively closer to the objective. The optical filter (111) removes scattered laser light from the light transmitted to the first detector array (118). In other less preferred embodiments, the focus sensor comprises an air gage, a capacitance gage, an astigmatic reflected spot, and a reflected displacement gage.

Figure 10:
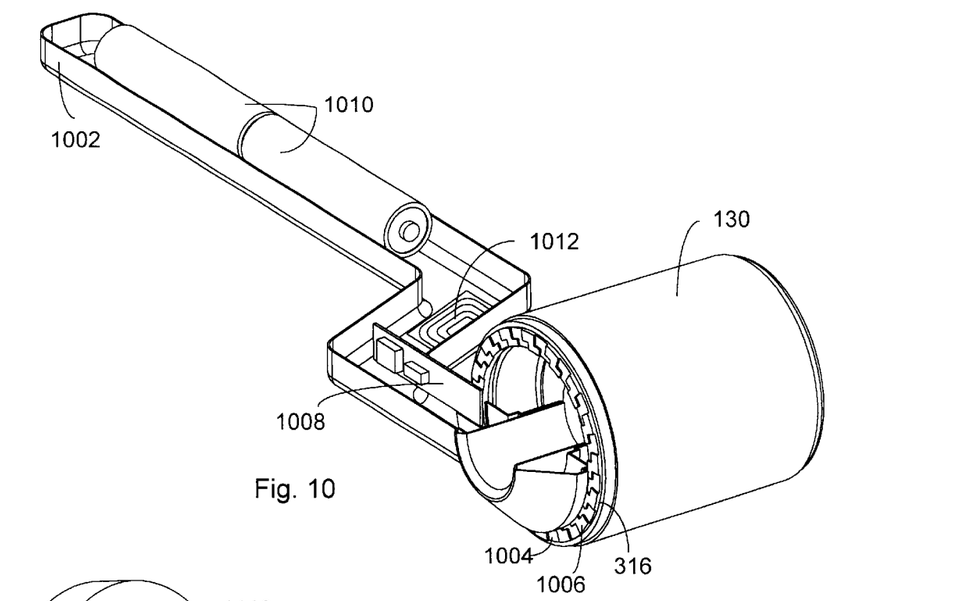
FIG. 10 shows a perspective view of an embodiment utilizing a flying spot scanner.

FIG. 10 shows the preferred embodiment of the handle means that senses rotation of the carrier of the tacky surface (130) as it is rolled across the test surface. Two concentric rings of hollows (1004) are etched into the externally facing surface of the bobbin (316), leaving a regular array of pads (1006) in quadrature. A printed circuit board (1008) with capacitive sensing circuit elements is positioned in the hollowed out handle (1002) in close proximity to the pads (1006), allowing the incremental position and direction of rotation of the bobbin to be sensed. Half of the hollowed out handle (1002) has been omitted for clarity. An RF antenna (1012) detects when the handle has been inserted in the positioning means and broadcasts the recent rotational history of the bobbin. This information is used by a fourth calculation means to interpret the measured particle counts as a particle aerial density. Batteries (1010) power the detection circuits, the RF generator, and the memory. The overall geometry of the handle means is generally mirror symmetric so that it is ambidextrous. In less preferred embodiments, rotation sensing is performed with one of the following: a Hall effect sensor, an incremental optical encoder, a motor generator, and a gear train. In less preferred embodiments rotation data is transmitted out of the handle means using one of the following: mating electrical contacts, capacitive contacts, and optical coupling.

The force applied by the handle means to press the tacky surface towards the test surface has some affect on the particle removal rates. To obtain more uniform results, an alternative preferred embodiment introduces compliance into the handle means to regulate the applied force. In an additional alternative preferred embodiment a force gage measures the applied forces as the tacky surface is being adhered to and removed from the test surface; these measured values are then reported to the controller in the same manner as the roller rotations just described.

ALTERNATIVE PREFERRED EMBODIMENTS

Scanned Laser Illumination

Figure 11:
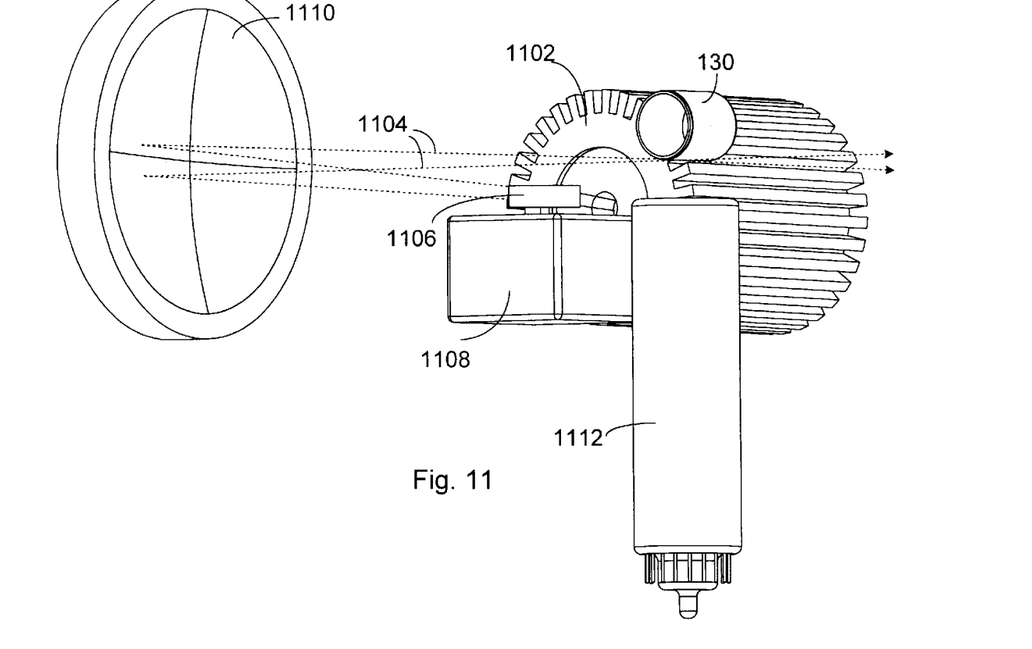
FIG. 11 shows a cut-away perspective view of a handle means with rotary motion detection and RF communication.

FIG. 11 shows an embodiment of the scanner means (100) that utilizes a flying laser spot. A solid state laser (1102) generates a beam (1104) that is swept by a moving mirror (1106) scanned by a galvo coil (1108) across a mirror (1110). The beam returning from the mirror comes to a focus as it grazes across the tacky surface; the position of the moving mirror determines the position of the laser on the tacky surface. A photomultiplier tube (1112) collects light scattered from surface features of the tacky surface.

Transfer Roller

Figure 12A:
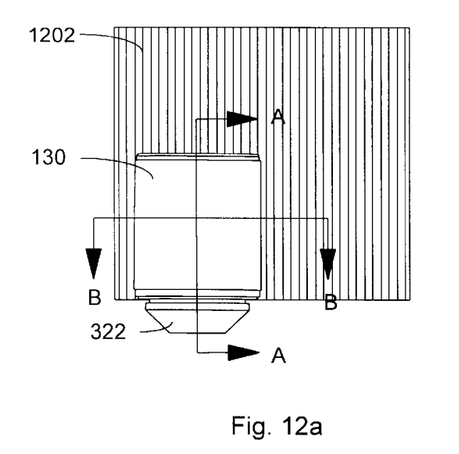
FIG. 12a is a plan view of an embodiment using an intermediate tacky surface for groove inspection.
Figure 12B:
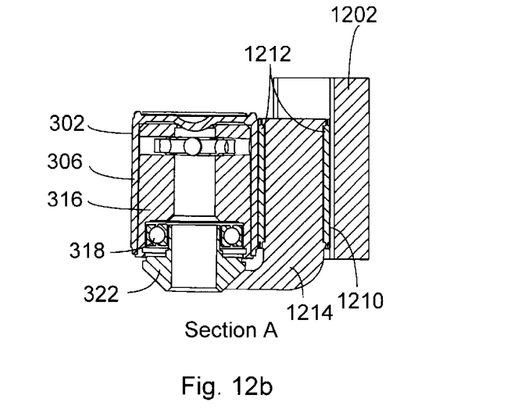
Figure 12C:
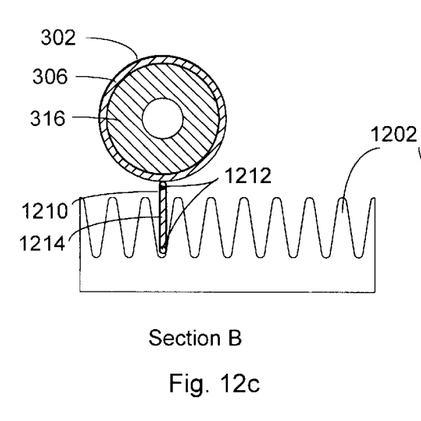
Figure 12D:
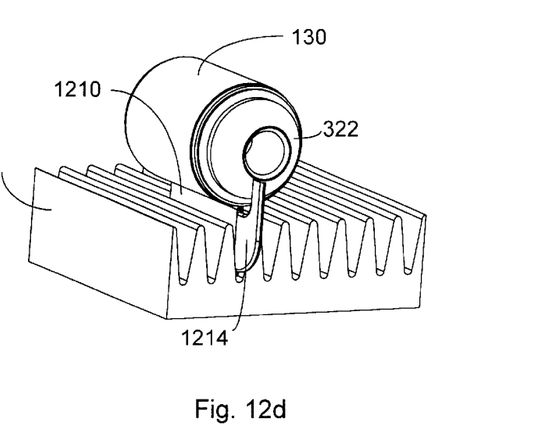
FIG. 12d is a perspective view of an embodiment using an intermediate tacky surface for groove inspection.

FIGS. 12a through 12d show an alternative preferred embodiment configured for inspecting high curvature surfaces such as the grooves supporting wafers in a semiconductor FOUP (1202). FIG. 12d is the perspective view. FIGS. 12b and c are cross sectional views from the plan view in FIG. 12a. A flexible tube of material with a tacky surface (1210) acts as a transfer roller between the surface of the grooved material (1202) and the carrier of the tacky sheet (130). The flexible tube is stretched around two bearing rollers (1212) separated by a guide plate (1214) attached to the button (322). As the handle means is manipulated to track the lower roller (1212) over the test surface, the tacky surface of the flexible tube progressively adheres to and releases from the test surface, transports particles from the test surface along the guide plate to the carrier of the tacky surface (130), adheres to and releases from the test surface, depositing particles from the test surface on the tacky surface (302), and continues to move on the rollers (1212) back to the test surface to repeat the process.

Flexible Tacky Sheet

Figure 13:
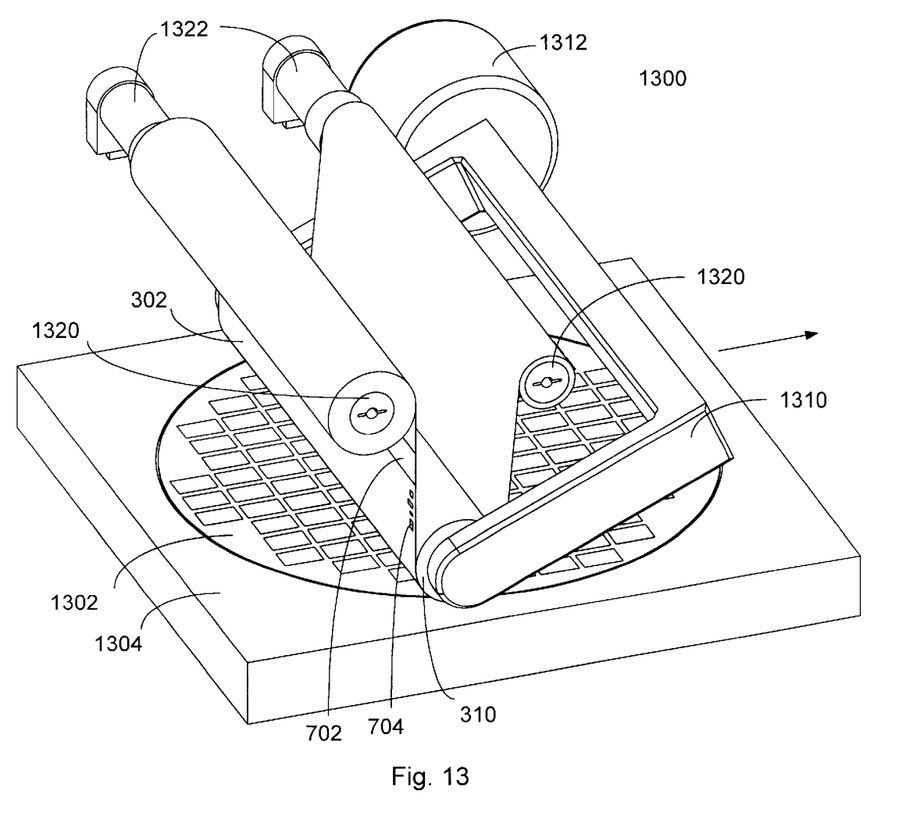
FIG. 13 is a perspective view of an embodiment using a flexible tacky sheet for in-situ cleaning and inspection.

FIG. 13 shows an alternative preferred embodiment adapted for in-situ inspection and cleaning in process tooling. A flexible sheet with a tacky surface (302) is dispensed from one cylindrical core (1320) and taken up by another cylindrical core (1320). Two servo motors (1322) control the tension and progression of the flexible sheet. A conformal roller (310) is supported by a frame (1310) on a motorized pivot (1312). Test surfaces (1302) to be inspected on support (1304) pass underneath the rollers as part of the manufacturing process flow. A sequence of alignment marks (704) and low-tack portions (702) along the tacky sheet allow a sequence of test surfaces to be rolled by the conformal roller (310) before the two cylindrical cores are removed and mounted in a surface inspection means and the tacky sheet is inspected.

In a less preferred embodiment, a polymeric material is applied in liquid form to the test surface and allowed to cure to form a film. The film is removed by rolling onto a cylindrical core (1320), which is then received by the positioning means. A polymeric material for this process comprises a hydrophilic polyurethane.

Adhesion modifiers can be usefully applied to all embodiments. Pre-treating a test surface with a corona discharge such as produced by adhesion enhancement products from Softal 3DT LLC increase the adhesion between the particles and the tacky surface. Applying vapor to the tacky surface as it is adhered to the test surface can improve the release between the tacky surface and the test surface.

Figure 14:
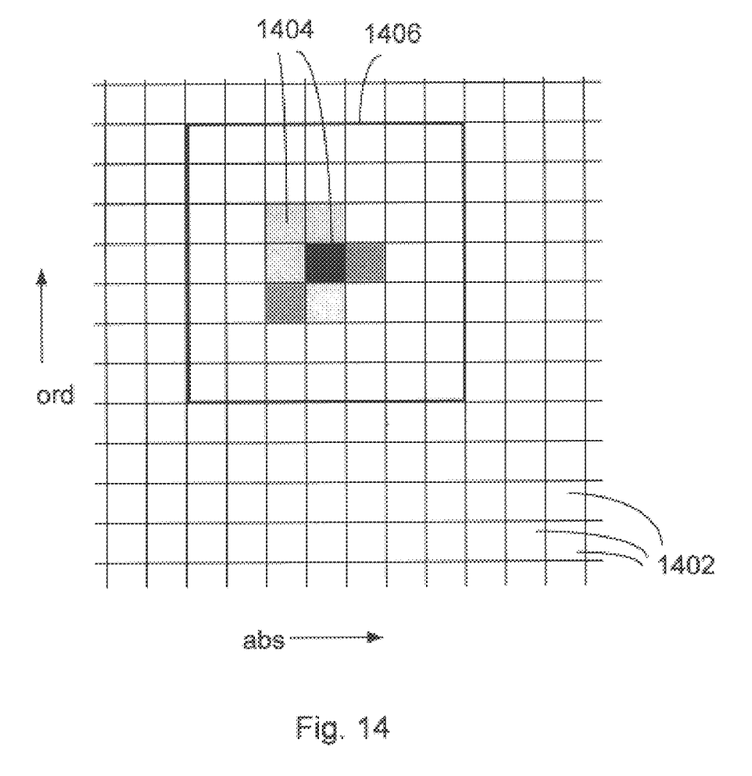
FIG. 14 shows pixels in the coordinate system of the tacky surface.

FIG. 14 shows a preferred calculation means for all of the embodiments. Each rectangle or pixel (1402) represents a possible location of a particle coordinate on the tacky sheet. The darkened rectangles or pixels (1404) represent particle coordinates associated with a single particle. Several pixels can be affected by a single particle if the particle is large, if the particle is close to the boundary between pixels, if the particle is out of focus, or if the particle is in a region of overlap between successive scans. Rather than reporting each pixel (1404) as an occurrence of a different particle, it is preferable to merge adjacent or nearly adjacent pixels. This can be done by the first calculation means, or in the most preferred embodiment as part of the output of the second calculation means.

Figure 15:
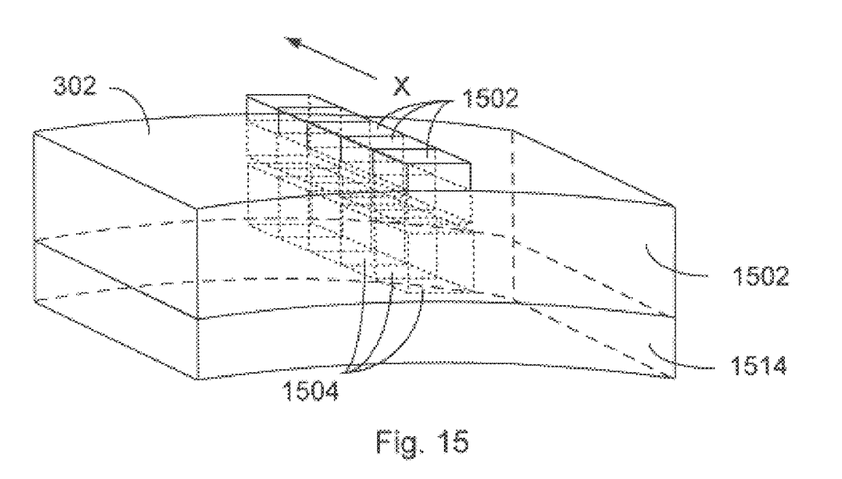
FIG. 15 shows voxels associated with two detector arrays as they would be imaged near the tacky surface.

FIG. 15 shows the image (1502) of the first detector array (118) at the tacky surface (302), and the image (1504) of the second detector array (124) below the tacky surface (302) in the bulk of the tacky material (1502). This is applicable to all preferred embodiments that utilize optical detection with at least two detector arrays. The primary purpose of the second detector array is to identify those light scatter events that become more intense with increasing depth from the tacky surface; these light scatter events are assumed to not be from particles transferred from test surfaces, and are ignored. The separation of the images of the two arrays normal to the tacky surface (302) should be at least a depth of focus for the sensing wavelength, numerical aperture of the objective, and index of refraction of the bulk of the tacky material (1502). If there is a buried interface between the bulk of the tacky material (1502) and a supporting layer (1514), the image of the second detector array (1504) should be above that interface. Less preferred embodiments for acquiring similar depth information include confocal microscopy, Nipkow wheels, and Linnick interferometry.

Although the present invention has been described with reference to preferred embodiments, workers skilled in the art will recognize that changes may be made in form and detail without departing from the spirit and scope of the invention. For example, the various features of most preferred embodiment may be used and interchanged with the alternative preferred embodiments, and vice-versa. These and other changes will be apparent to one skilled in the art.

What is claimed is:

1. A sampler for acquiring removable particles from a test surface and transporting them to a scanner means that detects coordinates of particles on a convex surface, the sampler being manipulated by an operator using a handle means having a rotary joint, the scanner means being capable of mechanically receiving the handle means, the scanner means being able to translate coordinates of particles with respect to alignment mark coordinates, comprising:

a carrier with a tacky convex surface, the carrier being generally cylindrical with an axial recess which mechanically engages the rotary joint in the handle means, the tacky convex surface adapted to transfer removable particles from the test surface to the tacky convex surface upon contact and subsequent separation therebetween while affording clean separation between the test surface and the tacky convex surface, whereby the operator adheres and removes a portion of the tacky convex surface from the test surface by manipulating the handle means engaged to the axial recess and rolling the tacky convex surface across the test surface, the operator transports the handle means engaged to the carrier to the scanner means, and the scanner means scans the carrier with the tacky convex surface by mechanically receiving the handle means engaged to the carrier; and an alignment mark proximate to the tacky convex surface, the alignment mark being configured to reproduce characteristics of a particle on the tacky convex surface and enabling the scanner means to detect the alignment mark coordinates in the manner that the scanner means detects the coordinates of a particle on the convex surface, whereby the scanner means detects coordinates of particles on the tacky surface, the scanner means detects alignment mark coordinates of the alignment mark proximate to the tacky surface, and the scanner means references the coordinates of particles with respect to the alignment mark coordinates.

2. The apparatus of claim 1, wherein the alignment mark comprises at least one of the following features: a deposited feature, a printed feature, a buried natural feature, a scribed feature, an ablated feature, and a reacted feature.

3. The apparatus of claim 1, further comprising a sequence of alignment marks proximate to the tacky surface, the relative spatial positions of the sequence of alignment marks forming encoded data.

4. A sampler for acquiring removable particles from a test surface and transporting them to a scanner means that detects coordinates of particles on a convex surface, the sampler being manipulated by an operator using a handle means having a rotary joint, the scanner means being capable of mechanically receiving the handle means, the scanner means being able to translate coordinates of particles with respect to alignment mark coordinates, comprising:

a carrier with a convex surface, the carrier being generally cylindrical with an axis and an axial recess capable of mechanically engaging the rotary joint in the handle means;

a tacky portion of the convex surface with an axial length, the tacky portion of the convex surface adapted to transfer initially removable particles from the test surface to the tacky portion of the convex surface upon contact and subsequent separation therebetween while affording clean separation between the test surface and the tacky portion of the convex surface, whereby the operator transfers initially removable particles from the test surface to the tacky portion of the convex surface by manipulating the handle means engaged to the axial recess and rolling the portion of the tacky convex surface across the test surface;

a low tack portion of the convex surface with less area than the tacky portion of the convex surface, the low tack portion of the convex surface adapted to negligibly adhere to the test surface, the low tack portion of the convex surface spanning the axial length of the tacky portion of the convex surface, whereby the operator detaches the convex surface from the test surface by manipulating the handle means engaged to the axial recess by first rolling the convex surface to an orientation where only the low tack portion of the convex surface contacts the test surface and then by moving the carrier away from the test surface approximately along the normal to the test surface; and an alignment mark proximate to the convex surface, the alignment mark being configured to reproduce characteristics of a particle on the convex surface and enabling the scanner means to detect the alignment mark coordinates in the manner that the scanner means detects the coordinates of a particle on the convex surface, whereby the operator transports the handle means engaged to the carrier to the scanner means, the scanner means scans the carrier with the tacky convex surface by mechanically receiving the handle means engaged to the carrier, the scanner means detects coordinates of particles on the tacky surface, the scanner means detects alignment mark coordinates of the alignment mark proximate to the convex surface, and the scanner means references the coordinates of particles with respect to the alignment mark coordinates.

5. The apparatus of claim 4, wherein the alignment mark is comprised of at least one of the following: a deposited feature, a printed feature, a buried natural feature, a scribed feature, an ablated feature, and a reacted feature.

6. The apparatus of claim 4, further comprising a sequence of alignment marks proximate to the convex surface, the relative spatial positions of the sequence of alignment marks forming encoded data.

7. The apparatus of claim 4, wherein the tacky portion of the convex surface comprises at least one of the following compositions: an acrylate pressure sensitive adhesive, a silicone pressure sensitive adhesive, and a rubber pressure sensitive adhesive.

8. The apparatus of claim 4, wherein the tacky portion of the convex surface comprises static dissipation means that reduces the surface resistivity of the tacky portion of the convex surface below $10^{12}$ ohms per square centimeter.

9. The apparatus of claim 4, further comprising a strippable protective film that isolates the tacky portion of the convex surface from contamination during storage and handling, whereby the strippable protective film is stripped from the tacky portion of the convex surface prior to the operator rolling the portion of the tacky convex surface across the test surface.

10. The apparatus of claim 4, further comprising a compliant and resilient polymeric foam cylindrical shell interposed between the carrier and the tacky portion of the convex surface.

11. A sampler for acquiring removable particles from a test surface and transporting them to a scanner means that detects coordinates of particles on a flexible sheet with an outer surface, the sampler being applied to the test surface by a manipulator means, the scanner means being able to translate coordinates of particles with respect to alignment mark coordinates, comprising:

a cylindrical core with a convex surface, an axis, and an axial recess, the axial recess allowing the cylindrical core to mechanically engage the manipulator means, the axial recess allowing the cylindrical core to mechanically engage the scanner means;

a flexible sheet with an inner surface and an opposing outer surface, a portion of the inner surface being adhered to a portion of the convex surface of the cylindrical core, the flexible sheet having an axial length parallel to the axis of the cylindrical core, the outer surface comprising a tacky portion and a low tack portion, the tacky portion of the outer surface adapted to transfer removable particles from the test surface to the tacky portion of the outer surface upon contact and subsequent separation therebetween while affording clean separation between the test surface and the tacky portion of the outer surface, the low tack portion of the outer surface adapted to negligibly adhere to the test surface, the low tack portion of the convex surface spanning the axial length of the flexible sheet; and an alignment mark proximate to the outer surface of the flexible sheet, the alignment mark being configured to reproduce characteristics of a particle on the flexible surface that are detected by the scanner means in the manner that the scanner means detects the coordinates of a particle on the flexible surface, whereby the manipulator means mechanically engages the cylindrical core, the manipulator means transfers initially removable particles from the test surface to the tacky portion of the outer surface by rolling the portion of the tacky outer surface across the test surface, the manipulator means detaches the tacky portion of the outer surface from the test surface by first rolling the outer surface to an orientation where only the low tack portion of the outer surface contacts the test surface and then by moving the cylindrical core away from the test surface approximately along the normal to the test surface, the scanner means receives the cylindrical core by mechanically engaging the axial recess, and the scanner means detects coordinates of particles on the tacky portion of the outer surface of the flexible sheet, the scanner means detects alignment mark coordinates of the alignment mark proximate to the outer surface flexible sheet, and the scanner means and references the coordinates of particles with respect to the alignment mark coordinates.

12. A method for acquiring removable particles from a test surface with a sampler and transporting them to a scanner means that detects coordinates of particles on a flexible sheet with an outer surface, the sampler being applied to the test surface by a manipulator means, the scanner means being able to translate coordinates of particles with respect to alignment mark coordinates, comprising:

engaging an axial recess of a cylindrical core with a manipulator means, the cylindrical core having a convex surface and an axis, a portion of the convex surface being adhered to a portion of the inner surface of a flexible sheet with an opposing outer surface, the outer surface comprising a tacky portion and a low tack portion, the tacky portion of the outer surface adapted to transfer removable particles from the test surface to the tacky portion of the outer surface upon contact and subsequent separation therebetween while affording clean separation between the test surface and the tacky portion of the outer surface, the low tack portion of the outer surface adapted to negligibly adhere to the test surface, the low tack portion of the convex surface spanning the axial length of the flexible sheet;

sampling particles on the test surface by rolling the outer surface in contact with the test surface and adhering the test surface to the tacky portion of the outer surface using the manipulator means;

removing the outer surface from the test surface by first rolling the outer surface to a configuration where the test surface is in contact with the low tack portion of the outer surface and the test surface is not in contact with the tacky portion of the outer surface, and then moving the cylindrical core away from the test surface approximately along the normal to the test surface; and engaging the axial recess of a cylindrical core with the scanner means, whereby the scanner means detects coordinates of particles on the tacky portion of the outer surface of the flexible sheet, the scanner means detects alignment mark coordinates of the alignment mark proximate to the outer surface flexible sheet, and the scanner means and references the coordinates of particles with respect to the alignment mark coordinates.

13. A method for acquiring removable particles from a test surface with a sampler and transporting them to a scanner means that detects coordinates of particles on a convex surface, the sampler being manipulated by an operator using a handle means with a rotary joint, the scanner means being able to translate coordinates of particles with respect to alignment mark coordinates, the scanner means being capable of mechanically engaging the handle means, comprising:

engaging the rotary joint of the handle means with an axial recess of a generally carrier with a convex surface, the convex surface having a tacky portion and a low tack portion, the tacky portion of the convex surface adapted to transfer removable particles from the test surface to the tacky portion of the outer surface upon contact and subsequent separation therebetween while affording clean separation between the test surface and the tacky portion of the convex surface, the low tack portion of the convex surface adapted to negligibly adhere to the test surface, the low tack portion of the convex surface spanning the axial length of the tacky portion of the convex surface;

sampling particles on the test surface by rolling the convex surface in contact with the test surface and adhering the test surface to the tacky portion of the convex surface by operator manipulation of the handle means;

removing the convex surface from the test surface by first rolling the carrier to a configuration where the test surface is in contact with the low tack portion of the convex surface and the test surface is not in contact with the tacky portion of the outer surface, and then moving the carrier away from the test surface approximately along the normal to the test surface; and engaging the handle means attached to the carrier with the scanner means, whereby the scanner means detects coordinates of particles on the convex surface of the flexible sheet, the scanner means detects alignment mark coordinates of the alignment mark proximate to the convex surface, and the scanner means references the coordinates of particles with respect to the alignment mark coordinates.

* * * * *